United States Patent
Zimmer et al.

(10) Patent No.: US 10,576,572 B2
(45) Date of Patent: Mar. 3, 2020

(54) METHOD AND DEVICE FOR MONITORING INERT GAS DURING A WELDING PROCESS

(71) Applicant: Fronius International GmbH, Pettenbach (AT)

(72) Inventors: Johannes Zimmer, Wels (AT); David Scharinger, Voecklabruck (AT); Manuel Gradauer, Inzersdorf (AT); Helmut Pfluegelmeier, Eferding (AT)

(73) Assignee: FRONIUS INTERNATIONAL GMBH, Pettenbach (AT)

( * ) Notice: Subject to any disclaimer, the term of this patent is extended or adjusted under 35 U.S.C. 154(b) by 219 days.

(21) Appl. No.: 14/647,484

(22) PCT Filed: Nov. 11, 2013

(86) PCT No.: PCT/AT2013/050215
§ 371 (c)(1),
(2) Date: May 27, 2015

(87) PCT Pub. No.: WO2014/082109
PCT Pub. Date: Jun. 5, 2014

(65) Prior Publication Data
US 2015/0298237 A1  Oct. 22, 2015

(30) Foreign Application Priority Data
Nov. 28, 2012  (AT) ............................... A 50547/2012

(51) Int. Cl.
*B23K 9/095*  (2006.01)
*B23K 9/32*  (2006.01)
(Continued)

(52) U.S. Cl.
CPC ............ *B23K 9/0956* (2013.01); *B23K 9/325* (2013.01); *B23K 9/328* (2013.01); *G01N 7/00* (2013.01); *G01N 25/20* (2013.01); *G01N 25/22* (2013.01)

(58) Field of Classification Search
CPC ...... B23K 9/0956; B23K 9/325; B23K 9/328; G01N 7/00; G01N 25/20; G01N 25/22
(Continued)

(56) References Cited

U.S. PATENT DOCUMENTS 4,095,080 A * 6/1978 Ueyama ................. B23K 9/164
219/137.41
6,091,048 A * 7/2000 Lanouette .............. B23K 9/095
219/130.21
(Continued)

FOREIGN PATENT DOCUMENTS

AT        504 964 B1    9/2008
DE        251305 A1     11/1987
(Continued)

OTHER PUBLICATIONS

Gabriel J. Duffy, Thermal Mass Flow Measurement, Aug. 2000, Dublin Ciry Univeristy, p. 26.*
(Continued)

*Primary Examiner* — Serkan Akar
*Assistant Examiner* — Chris Q Liu
(74) *Attorney, Agent, or Firm* — Collard & Roe, P.C.

(57) ABSTRACT

The invention relates to a method and a device (30) for monitoring the inert gas (5) during a welding process performed using a welding torch (7), wherein at least one measurement variable (Pi), which is dependent on the type of inert gas (5), is measured by means of at least one sensor (Si). According to the invention, at least two measurement variables (Pi) of the inert gas (5) are measured and the measured values (Mi) of the at least two measurement variables (Pi) of the inert gas (5) are compared with several stored values (Mi'), which are associated with inert gas types (Gi), of the at least two measurement variables (Pi), and the inert gas type (Gi), for which the assigned values (Mi') of the at least two measurement variables (Pi) are closest to the measured values (Mi) of the at least two measurement variables (Pi) of the inert gas (5), is displayed.

7 Claims, 4 Drawing Sheets

(51) Int. Cl.
*G01N 25/20* (2006.01)
*G01N 7/00* (2006.01)
*G01N 25/22* (2006.01)

(58) Field of Classification Search
USPC ...... 219/74, 137 R, 130.01, 136, 75, 130.21,
219/121.64, 121.72, 130.1, 121.55,
219/121.67, 121.83, 125.1, 130.33, 132,
219/137 PS, 108, 121.23, 121.44, 121.45,
219/121.46, 121.52, 121.63, 123, 130.5,
219/137.41, 137.42, 137.71, 137.9, 147,
219/602, 73.2; 73/25.01, 31.04
See application file for complete search history.

(56) References Cited

U.S. PATENT DOCUMENTS

| | | | | |
|---|---|---|---|---|
| 6,112,576 | A * | 9/2000 | Tsopelas | G01N 27/74 324/204 |
| 6,242,711 | B1 * | 6/2001 | Cooper | A61F 9/06 219/130.01 |
| 8,210,025 | B2 | 7/2012 | Eglseder et al. | |
| 2008/0149608 | A1 * | 6/2008 | Albrecht | B23K 9/0956 219/130.1 |
| 2010/0011837 | A1 * | 1/2010 | Eglseder | G01N 33/0037 73/29.02 |
| 2010/0276398 | A1 * | 11/2010 | Halvorsen | G05D 7/0635 219/74 |
| 2011/0163072 | A1 * | 7/2011 | Vogel | B23K 9/0953 219/74 |
| 2011/0284500 | A1 * | 11/2011 | Rappl | B23K 9/1006 219/74 |
| 2012/0269968 | A1 * | 10/2012 | Rayner, Jr. | C23C 16/452 427/255.26 |

FOREIGN PATENT DOCUMENTS

| | | |
|---|---|---|
| EP | 0 878 263 A1 | 11/1998 |
| WO | 2008/101264 A1 | 8/2008 |
| WO | 2009/031902 A1 | 3/2009 |

OTHER PUBLICATIONS

International Search Report of PCT/AT2013/050215, dated Mar. 3, 2014.

Austrian Office Action in A 50547/2012, dated Sep. 4, 2013, with English translation of relevant parts.

* cited by examiner

METHOD AND DEVICE FOR MONITORING INERT GAS DURING A WELDING PROCESS

CROSS REFERENCE TO RELATED APPLICATIONS

This application is the National Stage of PCT/AT2013/050215 filed on Nov. 11, 2013, which claims priority under 35 U.S.C. § 119 of Austrian Application No. A 50547/2012 filed on Nov. 28, 2012, the disclosure of which is incorporated by reference. The international application under PCT article 21(2) was not published in English.

The present invention relates to a method for monitoring the inert gas during a welding process performed using a welding torch, wherein at least one measurement variable, which is dependent on the type of inert gas, is measured by at least one sensor.

Furthermore, the invention relates to a device for monitoring the inert gas during a welding process performed using a welding torch, wherein at least one sensor for measuring at least one measurement variable, which is dependent on the type of inert gas, is provided.

While the subject matter of the application is directed to the monitoring of the inert gas during a welding process, the term inert gas also covers other gases used during welding processes, such as forming gases, process gases and transport gases.

Methods and devices determining the inert gas used in a welding process have been known from the prior art. For example, AT 504964 B1 describes a device and a method for measuring inert gas, wherein the protective effect of the inert gas is measured by determining the amount of oxygen of the inert gas.

WO 2009/031902 A1 shows the control of the flow of the inert gas in dependence on the welding current in order to obtain a gas flow, which is as constant as possible.

US 2011/163072 A1 describes a welding system and a method for controlling a welding device, wherein certain welding parameters, also including the optimum type of inert gas, are determined from certain set welding parameters, such as welding current and welding voltage, by means of drawing upon statistical analyses. The type of an inert gas used in a welding process cannot be determined.

Since determining the type of inert gas or its composition, e.g. with a chromatograph, is relatively complex, it has not yet been employed in welding devices.

It is therefore the object of the invention to provide the above-mentioned method and the above-mentioned device for monitoring the inert gas, which allows to draw conclusions as to the type of inert gas. It should be possible to realize the method and device in a manner as simple and cost-efficient as possible.

As regards the method, the object according to the invention is solved in that at least two measurement variables of the inert gas are measured and the measured values of the at least two measurement variables of the inert gas are compared with several stored values, which are associated with inert gas types, of the at least two measurement variables, and the inert gas type, for which the assigned values of the at least two measurement variables are closest to the measured values of the at least two measurement variables of the inert gas, is displayed. According to the invention, at least two measurement variables of the inert gas are measured and associated with the inert gas as a type of fingerprint. The measured fingerprint of the inert gas is then compared with stored fingerprints of known inert gases, and the inert gas type whose fingerprint corresponds closest to the fingerprint of the measured inert gas, is displayed on the display of the welding device. This means that, in the case of two measurement variables, one pair of values is formed and compared with stored pairs of values. When selecting easily measurable measurement variables of the inert gas, the method may be implemented in a relatively inexpensive and simple manner, thus enabling it to be also applied in a welding process or on a welding apparatus. Possible measurement variables of the inert gas include e. g. heating capacity, temperature, viscosity, density, critical flow (i.e. the flow in which there occurs a transition from laminar to turbulent flow) etc. The at least two measurement variables of the inert gas are measured under controlled conditions for the inert gases used in the welding technology and the values are associated with the respective inert gas type. Thus, a type of table, characteristic or map of the real inert gas types containing the respective associated values of measurement variables is created, stored and deposited as specification in the welding apparatus. The measured values for the at least two measurement variables of the inert gas are then compared in accordance with the specification, and the most likely inert gas type is selected and displayed on the welding apparatus. Thus, the welding operator can check the display of the welding apparatus to see which inert gas is being used in the welding process. Consequently, only those configuration options, which are possible with the selected inert gas, may be released for the welding operator. The welding apparatus automatically performs the releases, so as to facilitate the configuration for the welding operator.

Preferably, as measurement variables of the inert gas, the heating capacity and the differential pressure of the inert gas as measurement variable are measured, which serve as a measure for mass flow rate and volume flow rate, and the measured values of the heating capacity and of the differential pressure are compared with several stored values of the heating capacity and the differential pressure, which values are associated with the inert gas types, and the one inert gas type, for which the assigned values of the heating capacity and the differential pressure are closest to the measured values of the heating capacity and the differential pressure, is displayed.

The heating capacity and/or the mass flow rate of the inert gas may be measured in a particularly simple and inexpensive manner with a calorimetric mass flow measuring method. In this thermal flow meter, for instance, a heating element is heated in the path of the inert gas and the heat transport of the inert gas is detected with at least one temperature sensor. For this purpose, the sensor may also be integrated in the heating element. Such a calorimetric mass flow rate measuring method can be realized in a particularly simple and space-saving manner in thin-film technology. Equivalently, the temperature may also be kept constant and the current and/or the heating capacity may be measured accordingly to keep the temperature constant.

The differential pressure and/or the volume flow rate of the inert gas can suitably be measured on an orifice plate by means of sensors known from the prior art. Here, the volume flow rate is measured via the differential pressure as difference of the pressure of the inert gas on two locations. This measuring method may also be realized in a relatively simple manner and with a small size.

If comparing the measured values of the at least two measurement variables of the inert gas with stored values, which are associated with several inert gas types, of the at least two measurement variables does not yield a clear result and the associated stored values are equally far away from the measured values, the two inert gas types are preferably displayed. The welding operator may then select, on the display, the inert gas type which corresponds to reality or, if necessary, repeat the inert gas measurement.

An even more accurate determination of the inert gas may take place, if in addition the temperature of the inert gas is considered as a further measurement variable of the inert gas. Since many measurement variables of the inert gas, in particular also the heating capacity and the differential pressure, as a measure for the mass flow rate and the volume flow rate, depend on the temperature, this may be taken into consideration accordingly when detecting the temperature of the inert gas, and a more accurate measurement of the inert gas type may be carried out.

According to another feature of the invention, it is intended to issue a warning, whenever the differences of the measured values of the at least two measurement variables of the inert gas exceed threshold values of the stored values, which are associated to the several inert gas types, of the at least two measurement variables. If the measurement variables are too far away from the stored values and the result of the comparison would be too inaccurate, an acoustic or optical warning is issued to the welding operator or directly to the welding robot, calling for the measuring to be repeated.

If the flow rate and/or a return pressure of the inert gas is measured and it is detected that a given threshold value of the flow rate and/or of the return pressure of the inert gas is not reached, a warning of any possible contamination of the welding torch may be issued. In principle, the measurement of the inert gas may take place at any location in direct manner, or indirectly via the pressure of the inert gas. The measurement will be more accurate when the measurement takes place essentially within the welding torch, since the measurement takes place in the immediate vicinity of the contamination. However, a measurement in the welding torch, at a suitable location of the line from the gas storage to the welding torch, is also possible, the return pressure being detected and evaluated. In this connection, it is also advantageous to perform the measurements on a continuous basis during the welding process, so as to enable the generation of a pressure histogram and receive information concerning the contamination.

Advantageously, the welding torch is cleaned automatically whenever the adjusted threshold value of the flow rate and/or of the return pressure of the inert gas is not reached. For example, the robot can start a cleaning device, and the welding torch, in particular the gas nozzle thereof, may be cleaned of any impurities in a mechanical or magnetic manner.

The object according to the invention is also achieved by an above mentioned device for monitoring the inert gas during a welding process performed using a welding torch, wherein at least one sensor is provided for measuring at least two measurement variables of the inert gas, furthermore a memory for storing several inert gas types and values, which are associated with these inert gas types, of at least two measurement variables, an apparatus for comparing the measured value of the inert gas with the stored values associated with the several inert gas types, and a display for displaying the inert gas, whose associated values are closest to the measured values. Such a device is relatively easy to implement, in particular since devices which are present in welding apparatuses in any case, such as control devices, may be used for this purpose. As regards the other advantages of the monitoring device, reference is made to the above description of the method. For measuring the at least two measurement variables, a sensor can be used, which is capable of measuring both measurement variables, or also two sensors can be used for measuring one measurement variable of the inert gas in each case.

As mentioned, measuring the heating capacity and the differential pressure of the inert gas is particularly suitable as measurement variables.

In this connection, the sensor for measuring the heating capacity and/or the mass flow rate of the inert gas is preferably formed by a calorimetric mass flow rate sensor, which may be realized in thin film technology.

The sensor for measuring the differential pressure and/or the volume flow rate of the inert gas is preferably formed by at least one differential pressure sensor.

The display of the welding apparatus is designed to display two inert gas types, whose associated stored values of the at least two measurement variables of the inert gas are equally far away from the measured values of the at least two measurement variables of the inert gas. If the measured fingerprint of the inert gas is exactly in the middle of two stored fingerprints, both inert gas types are displayed on the display of the welding apparatus and the welding operator makes a selection or repeats the measurement.

If a sensor is provided for measuring the temperature of the inert gas as a further measurement variable of the inert gas, a more exact detection of the inert gas type may take place. The temperature of the inert gas may relatively easily be detected by means of sensors which can be miniaturized.

According to another feature of the invention, a warning device for emitting an optical and/or acoustic warning is provided, if the differences between the measured values of the at least two measurement variables of the inert gas and the associated stored values of the at least two measurement variables of the inert gas exceed preset threshold values. In this case, if the measured values deviate too much from the stored values or if the measured fingerprints of the inert gas deviate too much from the stored fingerprints, corresponding warnings will be emitted, which are to induce the welding operator or the welding robot to repeat the inert gas measurement.

The at least one sensor for measuring the at least two measurement variables of the inert gas is preferably arranged in a current source connected to the welding torch.

If, in addition, a sensor for measuring the flow rate and/or the return pressure of the inert gas is provided, whenever the measured flow rate and/or return pressure is less than a threshold value, this may imply contamination of the welding torch and a corresponding warning may be emitted to the welding operator or the welding robot.

It is of advantage to provide a cleaning device for the automatic cleaning of the welding torch, in case the at least one measured flow rate and/or return pressure of the inert gas is not reached. The cleaning device can perform a mechanical and/or magnetic cleaning of the components of the welding torch, in particular the gas nozzle thereof.

The present invention is described in more detail with reference to the enclosed, schematic drawings, in which.

Figure 1:
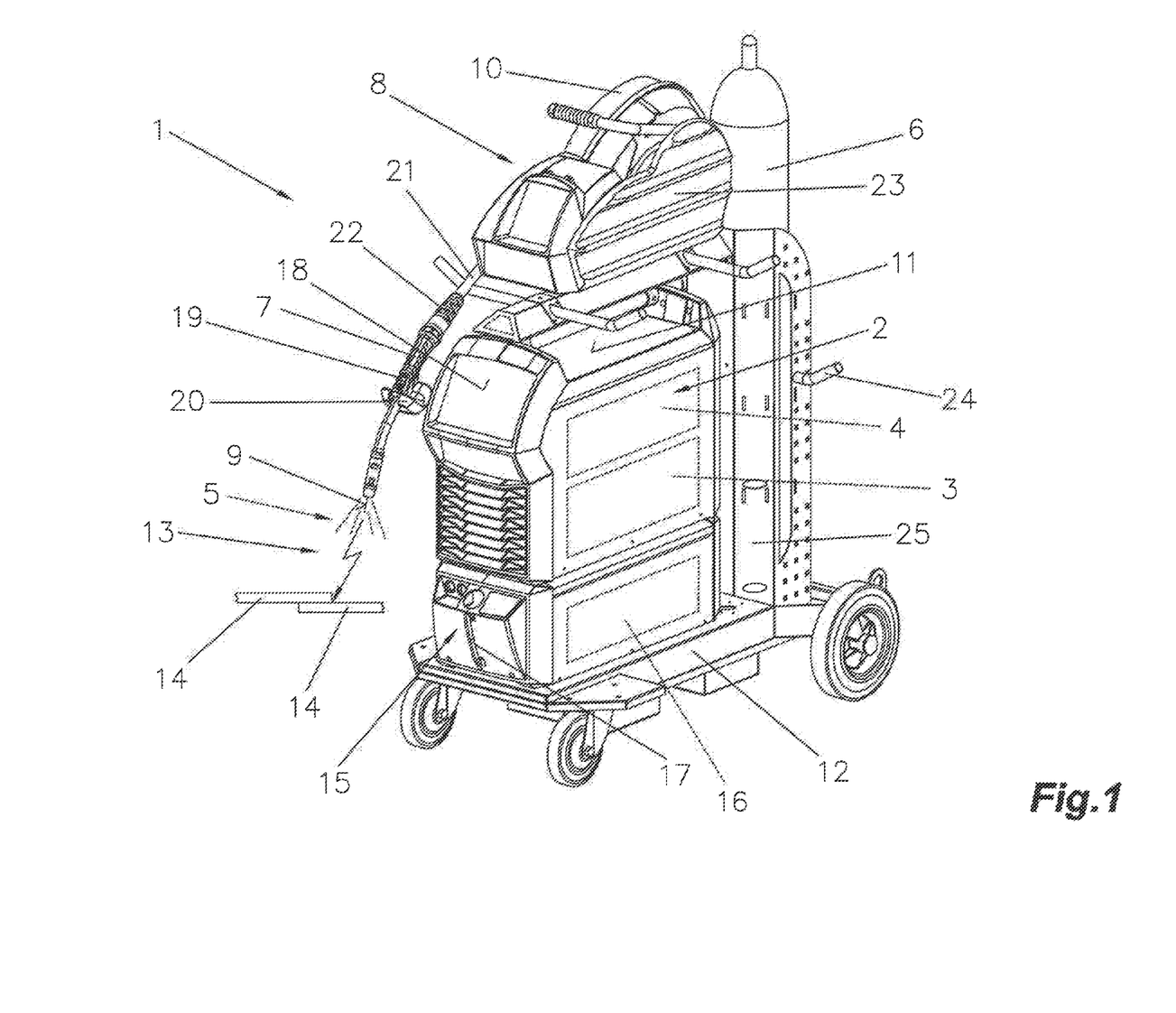
FIG. 1 is a schematic view of a welding apparatus.

In FIG. 1 a welding apparatus 1 for various processes or methods, such as MIG/MAG, WIG/TIG, electrode, double-wire/tandem welding methods, plasma or soldering methods, etc. is shown.

The welding apparatus 1 comprises a power source 2 comprising a power unit 3 arranged therein, a control means 4 and other components and lines (not shown), such as e. g. a switching element, control valves, etc. The control means 4, for example, is connected to a control valve, which is arranged in a supply line for an inert gas 5 between a gas storage 6 and a welding torch 7.

In addition, a device 8 for feeding a welding wire 9 from a supply drum 10 or a wire coil in the area of the welding torch 7 can be activated by the control means 4, for example, as is common in MIG/MAG welding. Of course, the feed device 8 can also be integrated in the welding apparatus 1, in particular in the housing 11 of the power source 2, and not be positioned—as shown in FIG. 1—as an additional device on a carriage 12. The feed device 8 for the welding wire 9 can also be placed directly on the welding apparatus 1, wherein the housing 11 of the power source 2 is designed on the top surface for receiving the feed device 8 and the carriage 12 can be omitted.

The welding wire 9 may also be supplied from a feed device 8 outside the welding torch 7 to the process point, wherein a non-melting electrode is preferably arranged in the welding torch 7, such as is common in WIG/TIG welding.

The current for establishing an electric arc 13 between the welding wire 9 and a work piece 14, which is made up of one or several parts, is supplied from the power unit 3 of the power source 2 to the welding torch 7 via a welding line (not shown). The work piece 14 is connected to the power source 2 via another welding line (not shown) for the further potential, in particular a mass cable, it thus being possible to build up, via the electric arc 13, an electric circuit for a process.

For cooling the welding torch 7, the latter is connected, via a cooling device 15, by means of interconnecting any possible components such as e. g. a flow monitor, to a container for liquids, in particular a water tank 16 comprising a level indicator 17. Upon starting up the welding torch 7, the cooling device 15, in particular a liquid pump used for the liquid disposed in the water tank, is started, thereby causing cooling of the welding torch 7. As may be seen in the shown embodiment, the cooling device 15 is positioned on the carriage 12, on which the power source 2 is placed subsequently. The individual components of the welding apparatus 1, i.e. the power source 2, the feed device 8 and the cooling device 15 are designed such that they have corresponding projections or recesses, so that they can safely be stacked on one another or put on top of each other.

The welding apparatus 1, in particular the power source 2 further comprises an input and/or output device 18, via which all kinds of different welding parameters, modes of operation or welding programs of the welding torch 1 can be adjusted and/or activated and displayed. The welding parameters, modes of operation or welding programs, which are adjusted via the input and/or output device 18, are passed on to the control means 4 and the individual components of the welding apparatus 1 are triggered thereby and/or corresponding set-points for the regulation or control are predetermined. When using a corresponding welding torch 7, adjustments may also be made via the welding torch 7, for which purpose the welding torch 7 is equipped with a welding torch input and/or output device 19. The welding torch 7 is preferably connected via a data bus, in particular a serial data bus, to the welding apparatus 1, in particular the power source 2 or the feed device 8. For starting the welding process, the welding torch 7 includes a start switch (not shown) in most cases, which upon being actuated will ignite the electric arc 13. To be protected against radiant heat dissipated by the electric arc 13, the welding torch 7 can be equipped with a heat shield 20.

In the shown embodiment, the welding torch 7 is connected to the welding apparatus 1 via a hose package 21, wherein the hose package 21 may be fastened to the welding torch 7 via an anti-kink element 22. The hose package 21 houses the individual lines extending from the welding apparatus 1 to the welding torch 7, such as e. g. the supply line, lines for the welding wire 9, the inert gas 5, the cooling circuit, the data transmission, etc., whereas the mass cable is preferred to be connected to the power source 2 separately. The hose package 21 is preferably connected to the power source 2 or the feed device 8 via a coupling device (not shown), whereas the individual lines in the hose package 21 are mounted to or in the welding torch 7 with an anti-kink element. To ensure a corresponding strain relief of the hose package 21, the hose package 21 may be connected to the housing 11 of the power source 2 or the feed device 8 via a cable relief means (not illustrated).

Basically, not all of the above mentioned components have to be used or employed for the different welding processes or welding apparatuses 1. The welding torch 7 may also be designed as air-cooled welding torch 7 and the cooling device 15 may be omitted. The welding apparatus 1 is formed of at least the power source 2, the feed device 8 and, at best, the cooling device 15, whereby these components may also be arranged in a joint housing 11. Other parts or components can be arranged, too, such as e. g. a wear protection 23 on the feed device 8 or an optional carrier 24 on a support means 25 for the gas storage 6, etc.

The embodiment of a welding apparatus 1 shown in FIG. 1 only constitutes one of many options. In particular, the welding apparatuses 1 may vary considerably with respect to the supply of the welding wire 9, the length of the hose package 21, the type, position and number of feed device 8 for the welding wire 9, the presence of a wire buffer (not shown) and much more.

Figure 2:
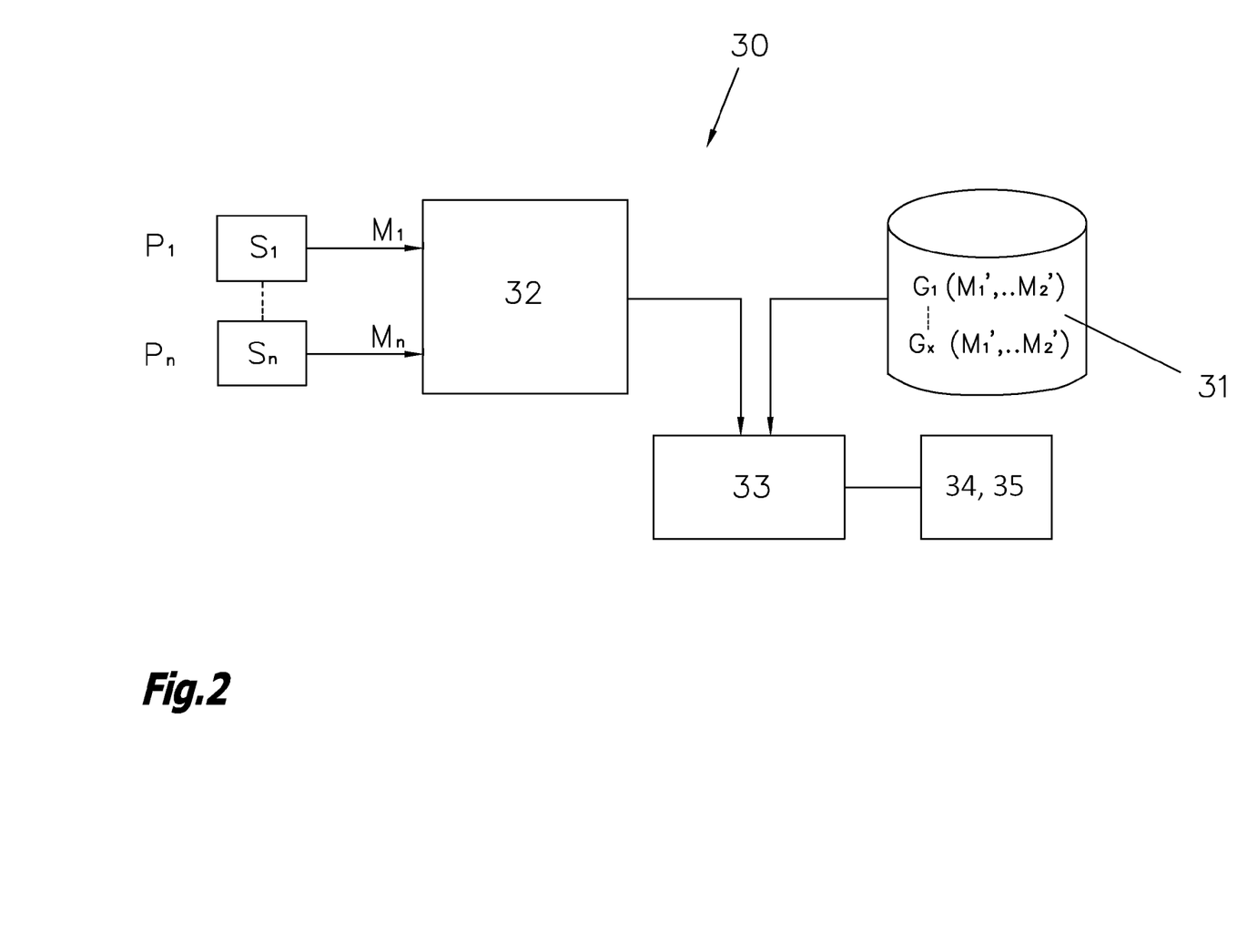
FIG. 2 is a block diagram of a method for monitoring the inert gas in a welding process.

FIG. 2 shows a block diagram to illustrate a method for monitoring the inert gas during a welding process performed using a welding torch, wherein at least two measurement variables Pi of the inert gas are measured by means of at least one sensor Si. In this connection, one sensor Si each can be employed for measuring one measurement variable Pi of the inert gas or a sensor Si for measuring several measurement variables Pi of the inert gas. The device 30 for monitoring the inert gas further comprises a memory 31, in which at least two measurement variables Pi are assigned to each inert gas type as measured values Mi' and stored. Upon a possible pre-processing in a corresponding device 32 of the measured values Mi, which are measured by the sensors Si, the measured values Mi are compared with the stored values Mi' in a comparator 33. In this connection, the measured values Mi represent the measured values of the measurement variable Pi. The at least one inert gas type Gi, whose assigned values Mi' come closest to the measured values Mi of the inert gas, is then displayed on a display 34. A warning device 35 emits an optical or acoustic warning if the difference between the measured values Mi of the at least two measurement variables Pi of the inert gas 5 and the associated stored values Mi' of at least two measurement variables Pi of the inert gas 5 exceed predetermined threshold values. The warning device emits a warning of contamination of the welding torch 7 in case the measured flow rate and/or the return pressure fall below a predetermined threshold value. The inert gas type detected also has an effect on the setting of parameters and/or configuration of the welding torch, in that e.g. only those characteristic lines can be selected which are possible with the inert gas type detected. This also applies to individual parameters, such as the material of the work piece material or the amperage. This means that the configuration possibilities are limited and/or given. As a measurement variable Pi of the inert gas, the heating capacity and the differential pressure of the inert gas are preferably measured as a measurement for the mass flow rate and the volume flow rate. The measurement depends on influence quantities, such as temperature T, viscosity, density p, heat conductivity, etc., whereby the influence quantities depend on the inert gas accordingly. Thus, correspondingly different measured values Mi of the measurement variables Pi of the inert gases result.

Upon assigning the inert gas prior to a welding procedure, the sensor is adjusted to the inert gas and can thus measure the mass flow rate and/or the volume flow rate during a welding procedure. Therefore, the preferred sensor used is a mass flow sensor.

Figure 3:
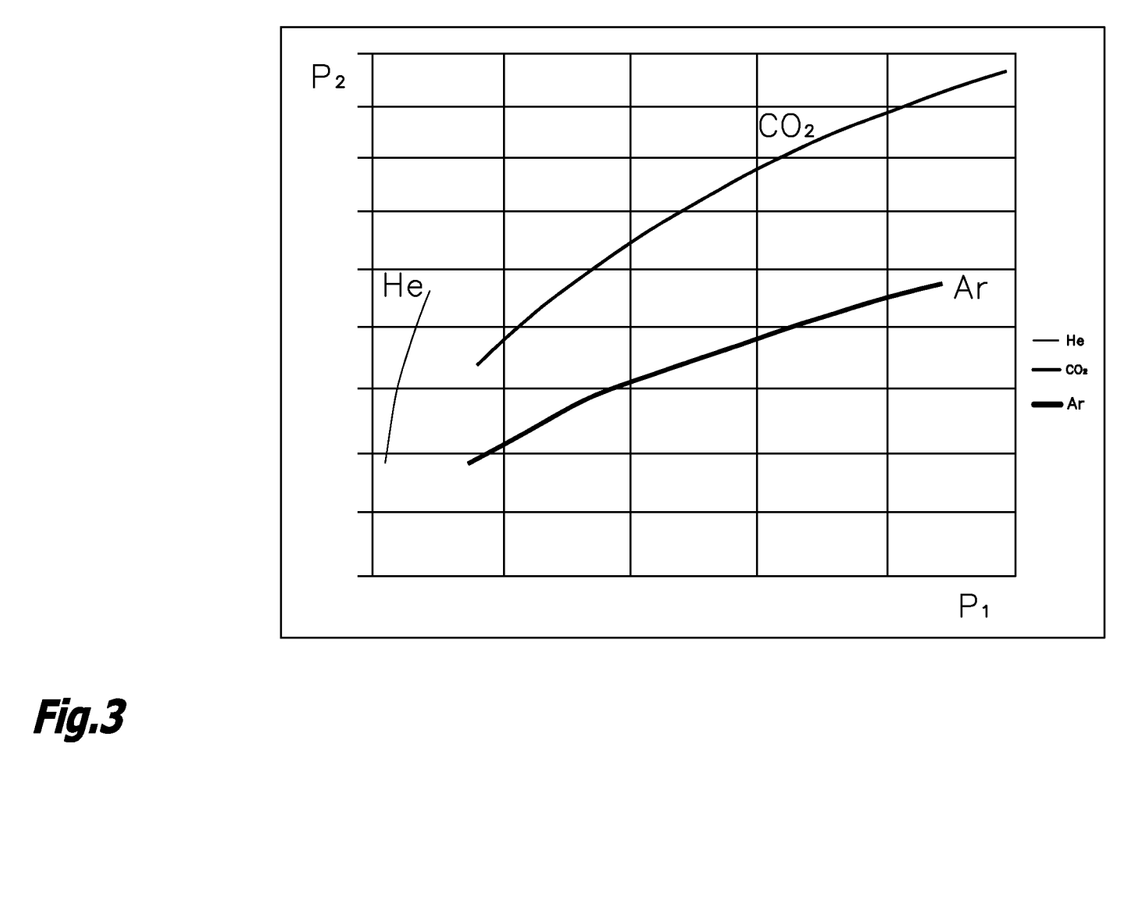
FIG. 3 is an example of a characteristic curve with several stored values, associated to inert gas types, of two measurement variables of the inert gas.

FIG. 3 shows an example of stored measured values, wherein the heating capacity and the differential pressure of an inert gas are plotted as the two measurement variables P1 and P2. The heating capacity is determined by means of a calorimetric mass flow sensor. The differential pressure is measured on an orifice plate, i. e. on a narrow. Under laboratory conditions or after calibration, the values of the measurement variables P1 and P2 are detected for the inert gases used in the welding method and the corresponding inert gas type is defined by a characteristic line. The measured values of the measurement variables P1 and P2 of the inert gas are compared with the stored values and the inert gas, which is closest to the measured values, is selected and displayed. In an equivalent manner, the heating capacity may be replaced by the measurement variable of temperature increase or the like. The heating element is operated, for example, at a constant temperature to save the values. The power required to keep the temperature constant with the inert gas flowing through is correspondingly proportional to the heat transport. In an equivalent manner, this can also be measured indirectly with the current for the heating element.

Figure 4:
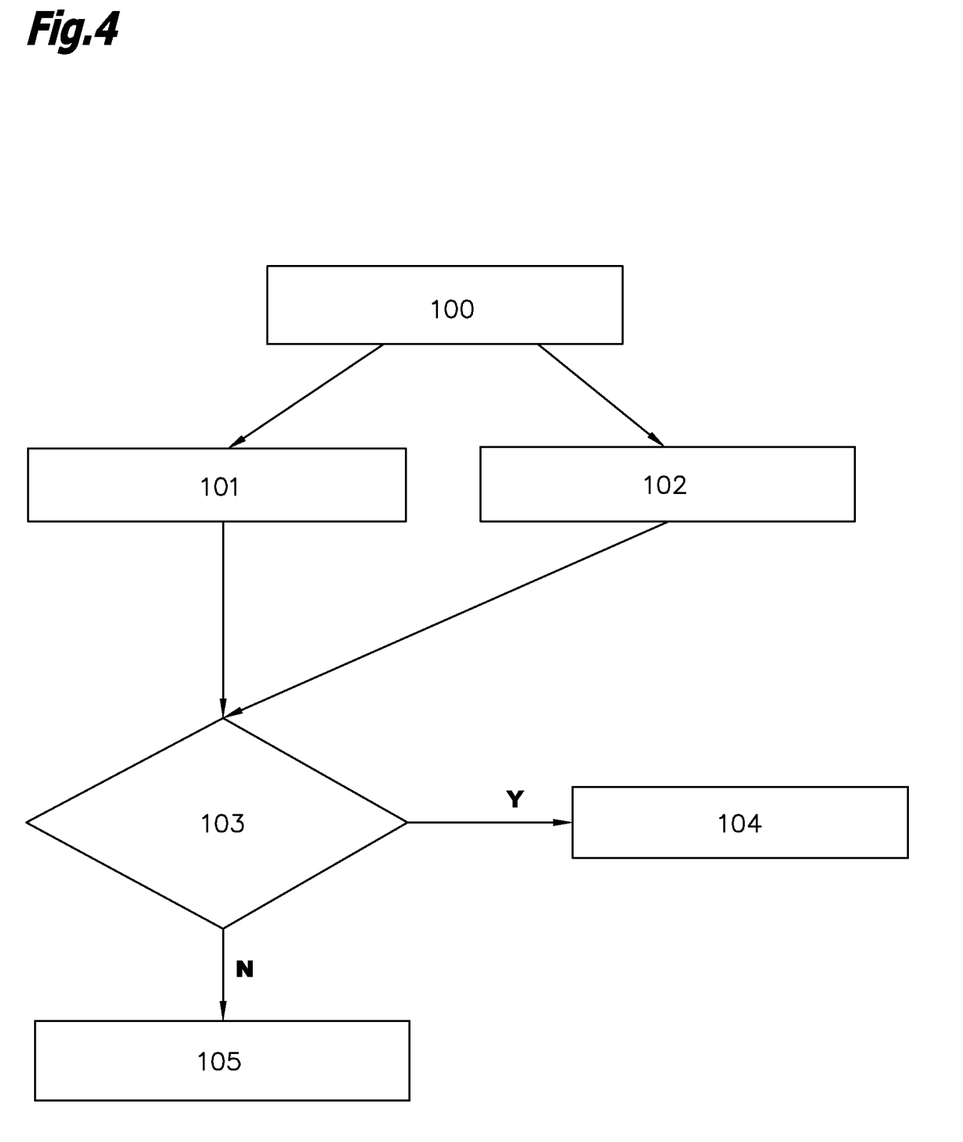
FIG. 4 is a block diagram for illustrating the detection of the flow of the inert gas as an indicator of a possible contamination of the welding torch.

FIG. 4 finally shows a flow diagram of a method, by means of which a conclusion can be made as to the contamination of the welding torch 7 or the gas nozzle thereof, by measuring the flow rate and/or the return pressure of the inert gas. After referencing the standard condition according to block 100 and a test for the pressure and/or flow rate measurement (block 102), the values of the pressure course and/or the flow course of the inert gas during the welding process are monitored and recorded in accordance with block 101. According to inquiry 103, the measured values are compared with a given threshold value. If the measured value is higher than the threshold value, the welding process is continued (block 104). If the measured value is smaller than or equal to the threshold value, the welding torch is subjected to a cleaning process (block 105), or at least a warning is emitted. After this, the welding process can be continued.

Hence, the pressure of the inert gas can be detected by means of the differential pressure, for one thing, and the return pressure, for the other.

The invention claimed is:

1. A method for monitoring inert gas for a welding process performed using a welding apparatus comprising a welding torch, the method comprising steps of:

storing values in a memory, the stored values being associated with several inert gas types, the stored values including respective heating capacities and respective differential pressures of the several inert gas types, supplying an inert gas to the welding torch, measuring a heating capacity of the inert gas via a mass flow sensor and a differential pressure of the inert gas via a differential pressure sensor to form measured values, comparing the measured values with the stored values, determining a type of the inert gas from the several inert gas types based on a first type of the several inert gas types having assigned values of the heating capacity and of the differential pressure closest to the measured values, displaying on a display said determined type of the inert gas, setting parameters or a configuration of the welding torch based on said determined type of the inert gas, after the setting of the parameters or the configuration, welding, via the welding torch, a workpiece, measuring a mass flow rate of the inert gas via the mass flow sensor during the welding, and emitting a warning concerning contamination of the welding torch when a predetermined threshold value of the mass flow rate of the inert gas is not reached.

2. The method according to claim 1, wherein the heating capacity of the inert gas is measured by a calorimetric mass flow rate measuring method.

3. The method according to claim 1, further comprising a step of:

measuring a temperature of the inert gas.

4. The method according to claim 1, further comprising a step of:

emitting a warning when differences of the measured values of the heating capacity and the differential pressure of the inert gas with respect to associated values of the values stored in the memory exceed predetermined threshold values.

5. The method according to claim 1, wherein the method further comprises steps of:

measuring a return pressure of the inert gas, and emitting a warning concerning contamination of the welding torch when a predetermined threshold value of the return pressure of the inert gas is not reached.

6. The method according to claim 5, further comprising a step of:

automatically cleaning the welding torch when the predetermined threshold value is not reached.

7. A method for monitoring inert gas for a welding process performed using a welding apparatus comprising a welding torch, the method comprising steps of:

storing values in a memory, the stored values being associated with several inert gas types, the stored values including respective heating capacities and respective differential pressures of the several inert gas types, supplying an inert gas to the welding torch, measuring a heating capacity of the inert gas via a mass flow sensor and a differential pressure of the inert gas via a differential pressure sensor to form measured values, comparing the measured values with the stored values, determining a type and an additional type of the inert gas from the several inert gas types based on a first type of the several inert gas types and a second type of the several inert gas types having two assigned values, respectively, of the heating capacity and of the differential pressure stored in the memory, when the two assigned values are equally far away from the measured values of the heating capacity and of the differential pressure of the inert gas, displaying on a display said determined type of the inert gas and said determined additional type of the inert gas, selecting on the display screen said determined type of the inert gas or said determined additional type of the inert gas to form a selected type, setting parameters or a configuration of the welding torch based on the selected type of the inert gas, after the setting of the parameters or the configuration, welding, via the welding torch, a workpiece, measuring a mass flow rate of the inert gas via the mass flow sensor during the welding, and emitting a warning concerning contamination of the welding torch when a predetermined threshold value of the mass flow rate of the inert gas is not reached.

* * * * *